United States Patent [19]

Nelson

[11] 4,307,073
[45] Dec. 22, 1981

[54] METHOD AND COMPOSITION FOR REDUCING THE TOXICITY OF ACETAMINOPHEN

[75] Inventor: Edward B. Nelson, Houston, Tex.

[73] Assignee: The Research Foundation of State University of New York, Albany, N.Y.

[21] Appl. No.: 176,418

[22] Filed: Aug. 8, 1980

[51] Int. Cl.³ .......................................... A61K 31/165
[52] U.S. Cl. ...................................... 424/10; 424/324
[58] Field of Search .......................... 424/324, 320, 10

[56] References Cited

U.S. PATENT DOCUMENTS 3,173,835  3/1965  Weiner et al. ...................... 424/324
3,317,377  5/1967  Hill et al. .......................... 424/324
4,017,614  4/1977  Wild ................................. 424/324
4,181,719  1/1980  Margetts et al. .................... 424/324

OTHER PUBLICATIONS

APhA Handbook of Nonprescription Drugs, 5th ed., (1977) pp. 120–133, Internal Analgesic Products (Acetaminophen Syrup Elixir Suspension Drops & Liquid).
U.S. Disp. 25th ed., (1955) Pt. I, pp. 1134–1135, "Propylene Glycol, USP".
C.A. 80#6793j, (1974) 78#53489h, (1973) 81#33115s, (1974) 89#190746a, (1978) 89#41137f #41138g #41139h, (1978) 80#67049t, (1974).

Primary Examiner—Shep K. Rose
Attorney, Agent, or Firm—Michael L. Dunn

[57] ABSTRACT

A method and composition for reducing the toxicity of acetaminophen to a warm blooded animal. The method comprises administering to the animal a sufficient dose of propylene glycol. The sufficient dose is an amount of from about 0.3 to about 12 grams per kilogram of body weight of the animal. The composition comprises a mixture of acetaminophen and propylene glycol preferably in a weight ratio of propylene glycol to acetaminophen of from about 0.3:1 to about 4000:1.

12 Claims, No Drawings

METHOD AND COMPOSITION FOR REDUCING THE TOXICITY OF ACETAMINOPHEN

TECHNICAL FIELD

This invention relates to analgesic pharmaceutical compositions and in particular relates to the toxicity of acetaminophen (4-hydroxyacetanilide).

BACKGROUND ART

Historically, there has been a search for methods for reducing pain in warm blooded animals and especially in human beings. The search for a safe, effective, analgesic composition, which can be administered to warm blooded animals, has therefore been a continuing one since better safety and effectiveness are always desirable.

One of the most common analgesic compositions for reducing pain is aspirin or sodium acetylsalicylate. Unfortunately, aspirin has some undesirable effects especially in some individuals who are sensitive to aspirin. This sensitivity can take the form of upset stomachs and G.I. disturbances and can be allergic reactions which in uncommon cases can even cause death.

For these reasons, acetaminophen, also known as 4-hydroxyacetanilide, was developed and is marketed as an analgesic for use by those who are sensitive to aspirin. Unfortunately, while acetaminophen seems to cause fewer gastro intestinal disturbances, the toxicity of acetaminophen is undesirably high and liver damage and even death can result from ingestion of excessive quantities of acetaminophen. While some approaches have been made to reduce the toxicity of acetaminophen, none of these approaches have been very successful. Some of the problems encountered in reducing the toxicity of acetaminophen are high costs, insufficient effectiveness, reduction of analgesic effect and the use of chemicals which themselves present toxological problems.

DISCLOSURE OF INVENTION

In accordance with the invention, there is provided a method for reducing the toxicity of acetaminophen to a warm blooded animal which is exposed in vivo to an excessive quantity of acetaminophen. The method comprises, within four hours of exposure to acetaminophen, administering a dose of propylene glycol to the animal. The dose is in an amount of from about 0.15 to about 12 grams per kilogram of body weight of the animal and preferably 0.3 to about 10 grams per kilogram of body weight of the animal. The invention further comprises a composition comprising a mixture of acetaminophen and propylene glycol.

The method and composition of the invention overcome essentially all problems, previously mentioned, associated with detoxification of acetaminophen. The method is exceedingly effective, the cost of the method and composition is very low, evidence indicates that there is little or no reduction in analgesic effectiveness of the acetaminophen as a result of utilization of the method or composition of the invention and in fact, there may be some enhancement of analgesic effect and the propylene glycol compound used to accomplish the detoxification of acetaminophen is itself known to be non-toxic.

BEST MODE FOR CARRYING OUT THE INVENTION

As previously discussed, the method in accordance with the present invention for reducing the toxicity of acetaminophen to a warm blooded animal exposed in vivo to an excessive quantity of acetaminophen, comprises administering propylene glycol to the animal. The administering of the propylene glycol, i.e., detoxifying compound, is usually done within four hours and preferably within two hours of exposure to the acetaminophen. The sooner that the detoxifying compound is administered, the greater effect of the compound. Most desirably, in order to avoid toxological effects, the detoxifying compound is administered simultaneously with the acetaminophen. In order to accomplish such simultaneous administration, the acetaminophen and the detoxifying compound, i.e., propylene glycol, are compounded together in a single drug composition such as an elixir. Propylene glycol also has the advantage of being a solvent for acetaminophen.

The detoxifying compound may be administered by any suitable method. For example, the compound may be administered orally, intraperitoneally, subcutaneously, intravenously or intra-muscularly. In general, the most preferred method for administering both the acetaminophen and the detoxifying compound, whether in the form of the composition or otherwise, when tests are not being conducted, is orally. Intravenous or intraperitoneally administration may be preferred when rapid absorption is required.

In general, a sufficient dose of the detoxifying compound is in an amount of from about 0.15 to about 12 grams per kilogram of body weight of the animal, preferably from about 0.3 to about 10 grams per kilogram of body weight of the animal and most preferably between about 0.3 and about 6 grams per kilogram of body weight of the animal. Furthermore, the sufficient dose of the detoxifying compound by weight should be between 0.2 and 4000 times the dose of acetaminophen, preferably between 0.3 and 4000 times the dose of acetaminophen and most preferably between 10 and 1000 times the dose of acetaminophen.

When the acetaminophen and detoxifying compound are administered simultaneously, the composition in accordance with the present invention is particularly suitable for this purpose. As previously discussed, the composition in accordance with the present invention comprises a mixture of acetaminophen and propylene glycol. The composition in accordance with the invention usually contains a weight ratio of propylene glycol to acetaminophen of from about 0.2:1 to about 4000:1, preferably contains a weight ratio of propylene glycol to acetaminophen of from 0.3:1 to about 4000:1 and most preferably contains a weight ratio of propylene glycol to acetaminophen of from about 10:1 to about 1000:1.

The detoxifying compound, may be diluted with at least one inert pharmaceutical carrier or diluent such as water, normal saline solution, talc, starch, gum acacia, magnesium stearate, lactose, sucrose, calcium phosphate, vegetable or mineral oils or waxes, methyl cellulose and ethanol. The composition may also contain an active pharmaceutical ingredient such as acetylsalicylic acid or sodium acetylsalicylate, aluminum aspirin, aspirin anhydride, caffeine and codeine phosphate. Essentially, any inert ingredient or active ingredient can be administered in combination with a composition of the invention provided adverse in vivo reactions or adverse chemical reactions do not occur as a result of the combination.

Similarly, essentially any inert ingredient, such as a filler, flavor, or color, can be administered in combination with a composition of the invention provided that no adverse reactions occur.

The following examples serve to illustrate and not limit method and composition of the invention.

EXAMPLE 1

Various doses of acetaminophen and propylene glycol are given simultaneously in 0.9% saline solution to white mice by intraperitoneal injection of 30 cc per kilogram of combined acetaminophen, propylene glycol and saline solution. Survivors are measured at 96 hours after dosage. The results are shown in Table 1.

TABLE 1

| Acetaminophen (A) | Propylene Glycol (P) | Ratio P:A | No. of Mice Tested | % Survival |
| --- | --- | --- | --- | --- |
| 400 mg/kg | none | 0:1 | 87 | 36 |
| 400 mg/kg | 30 mg/kg | 0.075:1 | 20 | 35 |
| 400 mg/kg | 300 mg/kg | 0.75:1 | 20 | 70 |
| 400 mg/kg | 1500 mg/kg | 3.75:1 | 20 | 80 |
| 400 mg/kg | 3000 mg/kg | 7.5:1 | 89 | 96 |
| none | 3000 mg/kg | 1:0 | 31 | 100 |

EXAMPLE 2

The procedure of Example 1 is repeated except that the doses are given orally. The results are shown in Table 2.

TABLE 2

| Acetaminophen (A) | Propylene Glycol (P) | Ratio P:A | No. of Mice Tested | % Survival |
| --- | --- | --- | --- | --- |
| 600 mg/kg | none | 0:1 | 32 | 19 |
| 600 mg/kg | 30 mg/kg | 0.05:1 | 17 | 0 |
| 600 mg/kg | 300 mg/kg | 0.5:1 | 20 | 50 |
| 600 mg/kg | 3000 mg/kg | 5:1 | 24 | 87 |
| 600 mg/kg | 6000 mg/kg | 10:1 | 16 | 87 |
| 600 mg/kg | 12000 mg/kg | 20:1 | 16 | 100 |
| 200 mg/kg | none | 0:1 | 8 | 87 |
| 200 mg/kg | 12000 mg/kg | 60:1 | 8 | 100 |
| 400 mg/kg | none | 0:1 | 8 | 12 |
| 400 mg/kg | 1200 mg/kg | 30:1 | 8 | 100 |
| 800 mg/kg | none | 0:1 | 8 | 0 |
| 800 mg/kg | 12000 mg/kg | 15:1 | 8 | 87 |
| none | 3000 mg/kg | 1:0 | 10 | 100 |
| none | 12000 mg/kg | 1:0 | 15 | 93 |

EXAMPLE 3

The procedure of Example 1 is repeated except that the propylene glycol is given orally and the acetaminophen is given intraperitoneally. The results are shown in Table 3.

TABLE 3

| Acetaminophen (A) | Propylene Glycol (P) | Ratio P:A | No. of Mice Tested | % Survival |
| --- | --- | --- | --- | --- |
| 400 mg/kg | none | 0:1 | 34 | 26 |
| 400 mg/kg | 6000 mg/kg | 15:1 | 14 | 92 |
| none | 6000 mg/kg | 1:0 | 15 | 100 |

EXAMPLE 4

The procedure of Example 1 is followed except the times from administration of the acetaminophen to administration of the propylene glycol are varied. The results are shown in Table 4.

TABLE 4

| Acetaminophen (A) | Propylene Glycol (P) | Time Difference | No. of Mice Tested | % Survival |
| --- | --- | --- | --- | --- |
| 400 mg/kg | none | | 10 | 0 |
| 400 mg/kg | 6000 mg/kg | simultaneous | 9 | 100 |
| 400 mg/kg | 6000 mg/kg | 2 hours | 20 | 50 |
| 400 mg/kg | 6000 mg/kg | 4 hours | 16 | 12 |

Examples 1 through 4 clearly demonstrate the dramatic effect of propylene glycol upon the acute toxicity of acetaminophen even with a substantial time lag between in vivo exposure to acetaminophen and treatment by administration of propylene glycol. The propylene glycol dosages can show effect in reducing toxicity of acetaminophen at as low as 300 milligrams (0.3 grams) per kilogram of body weight of mice or lower. Dosages of propylene glycol in excess of 12,000 mg/kg (12 grams/kg) do not appear warranted since higher concentrations of propylene glycol may themselves have a toxic effect. The most preferred range is from about 300 to about 6000 mg/kg (6 grams/kg) since propylene glycol does not appear to have a substantial toxic effect within that range. It is believed that even lower dosages, i.e., down to 150 or 200 mg/kg (1.5 or 2 grams/kg), of propylene glycol would be effective in humans since in general smaller dosages of drugs are required in large animals to have the same effect.

The ratio of propylene glycol to acetaminophen can be as low as 0.5:1 with substantial effect (see e.g. Example 2) although ratios much higher can be used and it is believed that higher ratios are limited only by the maximum safe dosage of propylene glycol that can be used, e.g., up to less than about 12,000 mg/kg, preferably up to about 10,000 mg/kg and most preferably up to about 6000 mg/kg. The preferred ratio of propylene glycol to acetaminophen is believed to be between about 4:1 to about 20:1. In general, the higher ratios are required for higher acetaminophen dosages.

EXAMPLE 5

In order to demonstrate the effect of propylene glycol upon the analgesic effect of acetaminophen, a mouse writhing test was used wherein 1% acetic acid is given intraperitoneally 5 minutes prior to counting abdominal writhes made by the animal. The dose of the 1% acetic acid given is 0.01 cc/gram of the body weight. 45 minutes before giving the acetic acid, the composition being tested for analgesic effect was given orally. The results are set forth in Table 5.

TABLE 5

| Drug Tested | No. of Mice Tested | No. of Writhes/ Per 5 min (mean ± S.D.) |
| --- | --- | --- |
| 1. Control (0.9% Saline) | 7 | 20.7 ± 4.4 |
| 2. 400 mg/kg acetaminophen in 0.9% saline | 9 | 8.4 ± 5.9 |
| 3. 10% propylene glycol in 0.9% saline | 16 | 16.7 ± 7.9 |
| 4. 400 mg/kg acetaminophen in 10% propylene glycol in 0.9% saline | 10 | 6.6 ± 4.3 |

The results set forth in Table 5 provide an indication that propylene glycol does not adversely affect the analgesic properties of acetaminophen and in fact may enhance such properties. Such conclusions are not, however, definite since the results of tests 1 and 3 are within statistical error as are the results of tests 2 and 4. The results set forth in Table 5 do show that if there is any adverse effect at all, it could be expected to be very small.

What is claimed is:

1. A method for reducing the toxicity of acetaminophen to a warm blooded animal exposed in vivo to an excessive quantity of acetaminophen which method comprises within four hours of said exposure administering to said animal a sufficient dose of a detoxifying compound consisting of propylene glycol, said dose being in an amount of from about 0.15 to less than about 12 grams per kilogram of body weight of the animal.

2. The method of claim 1 wherein the weight of the dose of the propylene glycol is between about 0.3 and 4000 times the weight of the dose of acetaminophen.

3. The method of claim 2 wherein the dose is from about 0.3 to about 10 grams per kilogram of body weight of the animal and the dose is administered in normal saline solution.

4. The method of claim 2 wherein the dose is administered orally.

5. The method of claim 3 wherein the dose is administered intraperitoneally.

6. The method of claim 3 wherein the dose is administered subcutaneously.

7. The method of claim 3 wherein the dose is administered intravenously.

8. The method of claim 3 wherein the dose is administered intramuscularly.

9. The method of claim 2 wherein the animal is exposed in vivo to acetaminophen by ingestion.

10. The method of claim 1 wherein the animal is exposed in vivo to acetaminophen and the administration of said compound occurs simultaneously.

11. The method of claim 2 wherein the animal is exposed in vivo to acetaminophen and the administration of said compound occurs simultaneously.

12. A composition consisting essentially of acetaminophen and propylene glycol.

* * * * *

UNITED STATES PATENT AND TRADEMARK OFFICE
CERTIFICATE OF CORRECTION

PATENT NO. : 4,307,073
DATED : Dec. 22, 1981
INVENTOR(S) : Edward B. Nelson

It is certified that error appears in the above—identified patent and that said Letters Patent are hereby corrected as shown below:

In Column 1 before "TECHNICAL FIELD" insert the following sentence:

--The invention claimed by this patent was sponsored under contract No. C-153219 awarded by New York State Health Research Council.--

Signed and Sealed this

Fourteenth Day of September 1982

[SEAL]

Attest:

GERALD J. MOSSINGHOFF

Attesting Officer

Commissioner of Patents and Trademarks